United States Patent
Yew et al.

(10) Patent No.: US 9,867,525 B2
(45) Date of Patent: Jan. 16, 2018

(54) HIGH SENSITIVITY TEMPORAL FOCUSING WIDEFIELD MULTIPHOTON ENDOSCOPE CAPABLE OF DEEP IMAGING

(75) Inventors: Yan Seng Elijah Yew, Singapore (SG); Heejin Choi, Brookline, MA (US); Vijay Raj Singh, Singapore (SG); Daekeun Kim, Seoul (KR); Jagath Rajapakse, Singapore (SG); Hanry Yu, Singapore (SG); Colin J. R. Sheppard, Singapore (SG); Peter T. C. So, Boston, MA (US)

(73) Assignees: NANYANG TECHNOLOGICAL UNIVERSITY, Singapore (SG); NATIONAL UNIVERSITY OF SINGAPORE, Singapore (SG); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1069 days.

(21) Appl. No.: 14/007,843

(22) PCT Filed: Apr. 2, 2012

(86) PCT No.: PCT/US2012/031839
§ 371 (c)(1),
(2), (4) Date: Jan. 8, 2014

(87) PCT Pub. No.: WO2012/135823
PCT Pub. Date: Oct. 4, 2012

(65) Prior Publication Data
US 2014/0128743 A1 May 8, 2014

Related U.S. Application Data

(60) Provisional application No. 61/470,577, filed on Apr. 1, 2011.

(51) Int. Cl.
*A61B 1/00* (2006.01)
*G02B 21/06* (2006.01)
(Continued)

(52) U.S. Cl.
CPC ...... *A61B 1/00172* (2013.01); *A61B 1/00163* (2013.01); *A61B 5/7203* (2013.01);
(Continued)

(58) Field of Classification Search
CPC .. A61B 1/00172; A61B 5/7203; G02F 1/3526
See application file for complete search history.

(56) References Cited

FOREIGN PATENT DOCUMENTS

EP     1283413 A1     2/2003

OTHER PUBLICATIONS

Yew et al., "Wide-field Two-photon Microscopy with Temporal Focusing and HiLo Background Rejection", Proc. SPIE 7903, Multiphoton Microscopy in the Biomedical Sciences XI, 79031O (Feb. 28, 2011).*

(Continued)

*Primary Examiner* — Alyssa M Alter
(74) *Attorney, Agent, or Firm* — Gesmer Updegrove LLP

(57) ABSTRACT

An imaging system is provided that includes a pulsed light source providing pulsed light and is applicable to both microscopes and endoscopes. One or more optical elements with certain dispersive properties are positioned to receive the pulsed light and apply selective dispersive properties to shift the focal plane according to the user and to produce two photon (2p) wide field uniform illumination and 2p wide field structured illumination for the purpose of improving the optical axial resolution and rejection of background signal. An imaging element receives the signal arising from the 2p wide field uniform illumination and 2p wide field structured illumination and produces a respective 3D resolved image of a sample.

21 Claims, 9 Drawing Sheets

(51) Int. Cl.
G02B 21/16 (2006.01)
G02B 23/24 (2006.01)
A61B 5/00 (2006.01)
G02F 1/35 (2006.01)
G01N 21/47 (2006.01)
G01N 21/64 (2006.01)

(52) U.S. Cl.
CPC ............ G02B 21/06 (2013.01); G02B 21/16 (2013.01); G02B 23/2423 (2013.01); G02B 23/2484 (2013.01); G02F 1/3526 (2013.01); *G01N 21/4795* (2013.01); *G01N 21/6458* (2013.01); *G02B 2207/114* (2013.01)

(56) References Cited

OTHER PUBLICATIONS

International Preliminary Report on Patentability dated Oct. 1, 2013 in connection with International Application PCT/US2012/031839, 8 pages.

International Search Report and Written Opinion of the International Searching Authority dated Jul. 13, 2012 in connection with International Patent Application No. PCT/US2012/031839, 13 pages.

Yew et al., "Wide-Field Two-Photon Microscopy with Temporal Focusing and HiLo Background Rejection", Proceedings of Spie, vol. 7903, Feb. 28, 2011, pp. 790310-790310.6.

Kim et al., "Three Dimensional (3D) High Speed Imaging and Fabrication System Based on Ultrafast Optical Pulse Manipulation", Proceedings of Spie, vol. 7183, Jan. 1, 2009, pp. 71831B-71831B-8.

Kim et al., "Axial Resolution for Two-Photon Wide Field Illumination Microscopy and Microfabrication", Proceedings of Spie, vol. 6860, Jan. 1, 2008, pp. 686028-686028-7.

Lim et al., "Optically Sectioned in Vivo Imaging with Speckle Illumination HiLo Microscopy", Journal of Biomedical Optics, vol. 16, No. 1, Jan. 1, 2011, p. 016014.

* cited by examiner

FIG. 2A
FIG. 2B
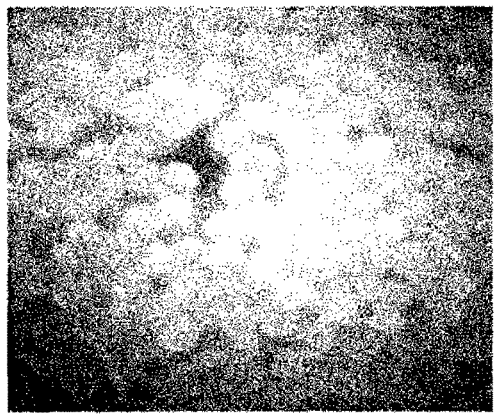
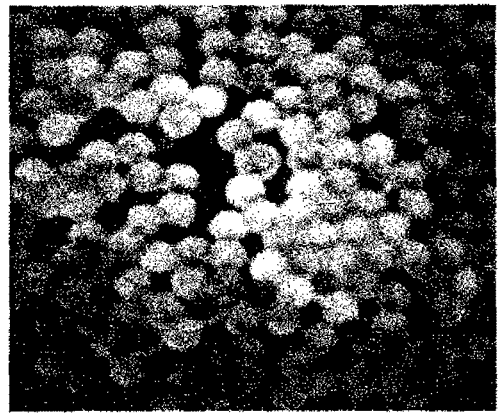
FIG. 3A
FIG. 3C
FIG. 3E
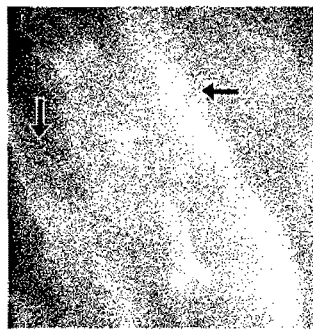
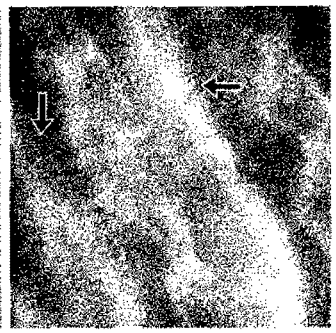
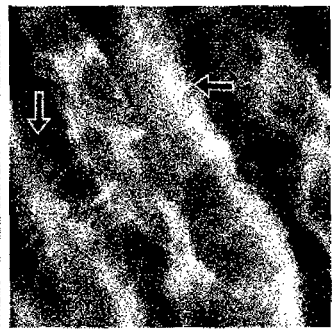
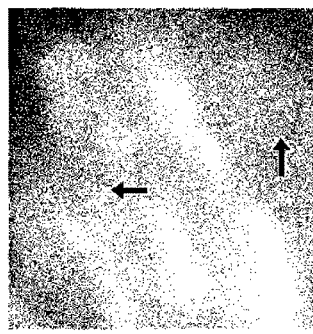
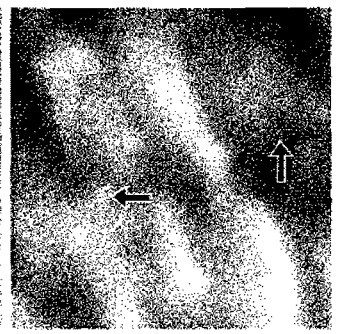
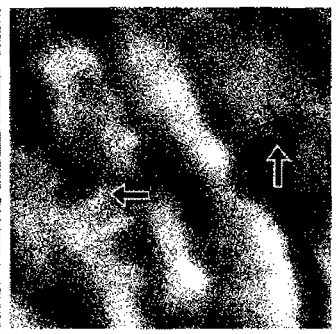
FIG. 3B
FIG. 3D
FIG. 3F

HIGH SENSITIVITY TEMPORAL FOCUSING WIDEFIELD MULTIPHOTON ENDOSCOPE CAPABLE OF DEEP IMAGING

PRIORITY INFORMATION

The present application is a 371 Application of PCT/US2012/031839 filed on Apr. 2, 2012 that claims priority to U.S. Provisional Application Ser. No. 61/470,577, filed on Apr. 1, 2011. Both applications are incorporated herein by reference in their entireties.

BACKGROUND OF THE INVENTION

The invention is related to the field of imaging using a system of dispersive and other optical elements to achieve a plane of high photon flux necessary for nonlinear optical processes to occur. This plane may be positioned at will along the optical axis through controlling the amount of dispersion in the beam. The illumination at the plane can be controlled to give uniform illumination and structured illumination for better contrast, rejection of background signal, and axial resolution. The invention is applicable to microscopes as well as endoscopes, and in particular a high sensitivity temporal focusing wide field multiphoton endoscope capable of deep imaging.

Traditional histological analysis is the clinical gold standard for cancer diagnosis but requires tissues to be excised, fixed, sectioned, stained and subsequently examined microscopically. Endoscopes allow for optical examination of tissues within the body cavity and complements traditional histological analysis of diseases. In certain cases, such as cancers occurring in the bronchial tree, excisional biopsy should be minimized and optical biopsy via endoscopy has the potential to guide excisional biopsy and to partly replace them. Moreover, optical biopsy is a powerful tool to determine the surgical margins during resection of cancerous lesions. Furthermore, nonlinear optical processes such as second-harmonic generation (SHG) are useful in examining extracellular matrix structures non-invasively. Studies have demonstrated its utility in the diagnosis of muscular dystrophy and in the diagnosis of ovarian cancer. Recent studies have demonstrated that it is possible to quantify the correlation between abnormally increased collagen fiber content fibrosis progression using optical means such as SHG.

SUMMARY OF THE INVENTION

According to one aspect of the invention, there is provided an imaging system. The imaging system includes a pulsed light source that provides pulsed light. One or more dispersive elements are positioned to receive the pulsed light and apply selective dispersive properties to recombine the spectrally dispersed pulse at a certain position along the optical axis where with the recombined pulse, a sequence of two photon (2p) wide field uniform illumination and 2p wide field structured illumination is generated at the focal plane. An imaging element receives multiple 2p wide field uniform illumination and 2p wide field structured illumination images to produce respective 3D resolved images of a sample.

In addition, optical elements are positioned such that either uniform illumination or structured (laternally patterned) illumination is generated. Furthermore, the method includes an imaging element receiving either the 2p wide field uniform illumination or 2p wide field structured illumination and producing a respective image of a sample. A computational algorithm combines the multiple uniform illumination and multiple structured illumination images to produce a 3D resolved optical section. This method allows for improving axial resolution, image contrast, and the rejection of background signal. Additionally, this algorithm may further "save" some of these rejected scattered photons by reassigning them to the correct image location using a maximum likelihood algorithm further improving image signal-to-noise (SNR) level.

BRIEF DESCRIPTION OF THE DRAWINGS

FIGS. 2A-2B are unprocessed and processed images illustrating the rejection of signals originating from out-of-focus planes;

FIGS. 3A-3F are processed images illustrating the background and removal of background from a two photon (2p) wide field image;

DETAILED DESCRIPTION OF THE INVENTION

Figure 1A:
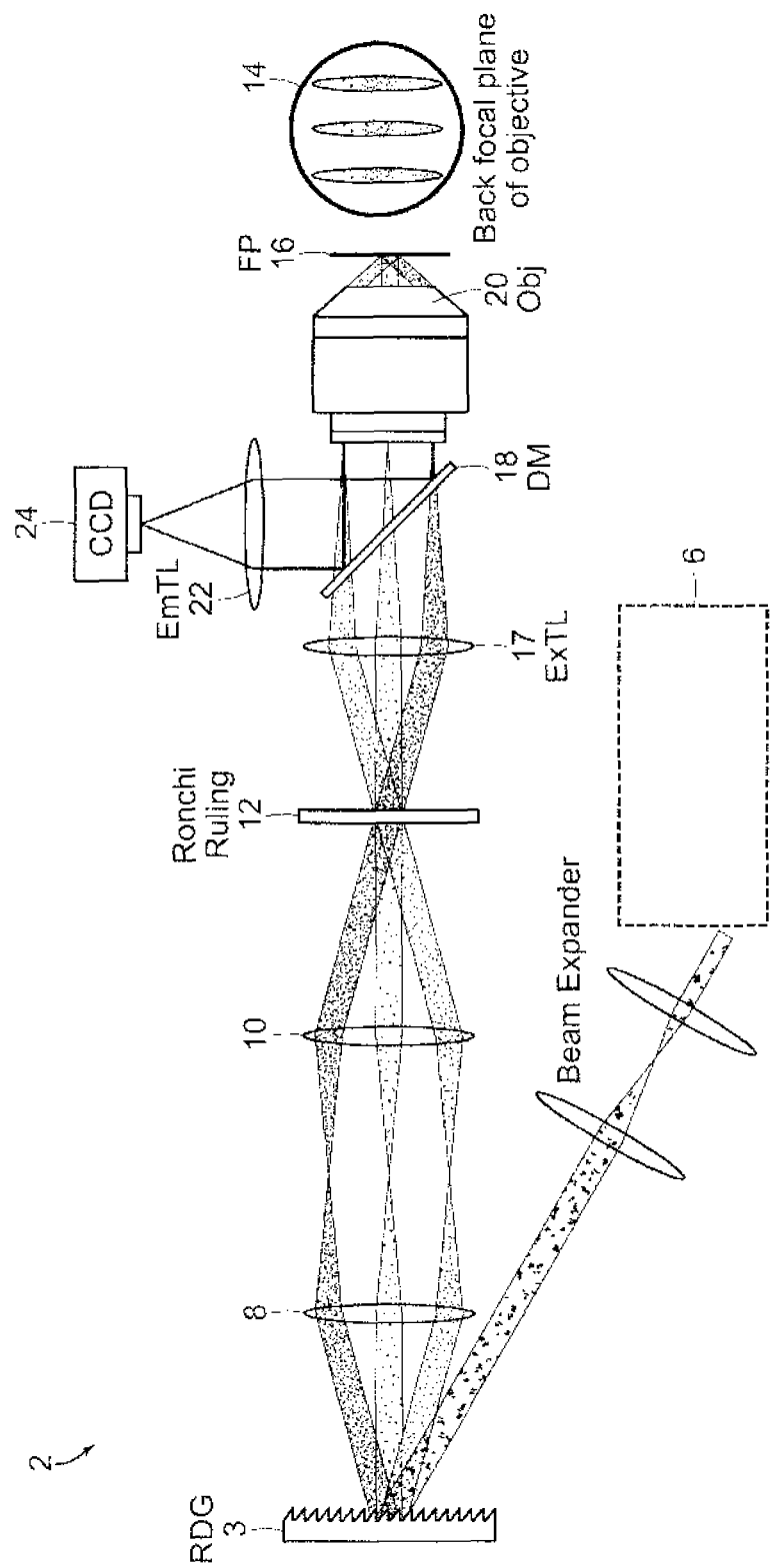
FIGS. 1A-1B are schematic diagrams illustrating arrangements used to produce structure light illumination.

The invention describes the combination of wide-field multiphoton imaging and structured light illumination and can be realized in a microscope or an endoscope format with applications in many minimally invasive diagnostic areas. Wide-field multiphoton imaging removes the need for MEMS actuators in the distal end resulting in an instrument that will be low cost, more robust and may provide higher imaging speed. However, conventional wide-field high speed imaging cannot image deep due to the presence of a uniform background from scattered photons; the incorporation of structured light illumination allows high sensitivity rejection of these out-of-focal plane signals.

The invention provides significant progress in demonstrating the feasibility of all these fronts. Specifically, scattered photons can be efficiently rejected with structured light illumination. Also, some of these rejected scattered photons can be "saved" by reassigning them to the correct image location using a maximum likelihood algorithm further improving image signal-to-noise level (SNR). The invention demonstrates that the scanning along all three axes can be eliminated from the distal end of the endoscope by showing that axial scanning can be readily accomplished by varying the spectral-phase relationship of the excitation pulses.

Axial scanning based on this approach has been shown by other groups but this approach has been implemented using a spatial light modulator allowing more facile depth control. Finally, the invention allows for the miniaturization of the whole system with micro-optics in an "open" design where performance can be evaluated at each stage. An enclosed design with a form factor less than 8 mm in diameter has been implemented and is being tested.

The invention proposes a multiphoton endoscope with high sensitivity that is capable of deep tissue imaging. To this end there is a source capable of generating ultrashort optical pulses with high pulse energy within a spectral bandwidth. This light is then delivered into the imaging system which includes one or more dispersive elements that disperse the incident light into a spectrum. The spectrum is then focused at the back focal plane of an objective which collimates each spectral component and recombines them only at the focal plane where the original pulse width is restored.

The group velocity dispersion (GVD) can be tuned to induce a quadratic spectral phase, which effectively shifts the focal plane and thereby creates scanning in the axial direction. The detected signal is relayed back through the imaging elements and separated from the excitation wavelengths by a dichroic filter. The absence of a scanning mechanism in the endoscope head allows for the incorporation of the detecting sensor within the endoscope head itself and increases the signal-to-noise ratio.

Wide field imaging techniques have the advantage of being fast. However, most utilize brightfield or single-photon fluorescence, which limits their applicability due to the lack of optical sectioning. Recently, temporal focusing makes possible wide field 2p imaging with the advantage of optical sectioning and deeper penetration due to reduced scattering and absorption when imaging into highly scattering media such as biological tissue. However, a major limitation of temporal focusing based 2p microscope for deep tissue imaging is image degradation in terms of the contrast loss due to the scattering of emission photons. Unlike the single-point scanning two-photon microscopy that is insensitive to emission photon scattering, the temporal focusing 2p microscope uses imaging detectors, such as CCDs and CMOSs, where the scattered emission photons contribute to uniform background resulting in a reduction of image signal to background ratio.

The structured light illumination in temporal focusing 2p microscopy can effectively reject these scattered emission photons and thereby improves image contrast for deep tissue imaging. For standard wide field single-photon microscope, a class of depth resolved imaging techniques based on structured light illumination (SI) has been proposed to select a particular imaging plane and to reject out-of-focus background. One of these classes of techniques, called HiLo microscopy, is unique in the sense that it combines the in-focused high frequency content extracted from the uniformly illuminated image (UI) and the in-focus low frequency content extracted from the structured light illuminated image (SI) to generate an optically sectioned image. This is different from the demodulation algorithm used in the prior art which requires at least three phase shifted images for the optically sectioned image.

Most importantly, the HiLo approach is relatively insensitive to motion artifacts that are present in endoscopic applications due to physiological noises. While these techniques are able to improve image contrast, the loss of out-of-focal plane photons limits the final image signal-to-noise ratio (SNR). Additionally, if the contrast of the projected grid is low this reduces the modulation and provides the weaker sectioning capability and as a result reduces the photons of the reconstructed optically sectioned image. The photon reassignment method seeks to better utilize the lost photons by using the 'prior knowledge' about the optical transfer function of the structured light illumination. By utilizing a maximum likelihood approach, the most likely fluorophores distribution in 3D can be identified that will produce the observed image stacks under structured and uniform illumination using an iterative maximization algorithm.

The invention generates SI by projecting through a grid as well as by interfering two plane waves at the focal plane using a Michelson interferometer setup and uses a photon reassignment method for 3D image reconstruction.

FIG. 1A shows the schematic of the experimental setup based on a grid projection 2. The grid projection 2 includes a reflective diffractive grating (RDG) 3 that disperses pulsed light received from a pulsed laser source 6 through a beam expander of variable magnification (BE) 26 into a spectrum. The pulse laser source 6 can include an ultrafast optical Ti:Sapphire laser 6. Lens structures 8, 10 focus the spectrum provided by RDG 3 to a Ronchi Ruling element 12 that receives the spectrum and performs further dispersion. An excitation tube lens (ExTL) 17 is positioned to receive the spectrum produced by the Ronchi Ruling element 12 and acts as a collimating lens. The focused spectrum from the ExTL 17 passes through a dichroic mirror element (DM) 18 and is received by an objective 20. The spectrum is then focused at the back focal plane 14 of an objective (Obj) 20 which collimates each spectral component and recombines them only at the focal plane (FP) 16 where the original pulse width is restored. The Ronchi Ruling element 12 is placed at the conjugate plane of both the RDG 3 and the focal plane 16 of the objective 20.

The group velocity dispersion (GVD) can be tuned to induce a quadratic spectral phase, which effectively shifts the focal plane and thereby creates scanning in the axial direction. A detected signal arising from within the object volume is relayed back through objective 20 and separated from the excitation wavelengths by the DM 18. The emission tube lens (EmTL) 22 focuses the detected signal on to a charged coupled device camera (CCD) 24 for imaging. The absence of a scanning mechanism in the endoscope head allows for the incorporation of the detecting sensor, such as the CCD 24 within the endoscope head itself and increases the signal-to-noise ratio.

To produce uniform illumination in the grid projection 2, one can remove the Ronchi Ruling element 12.

Figure 1B:
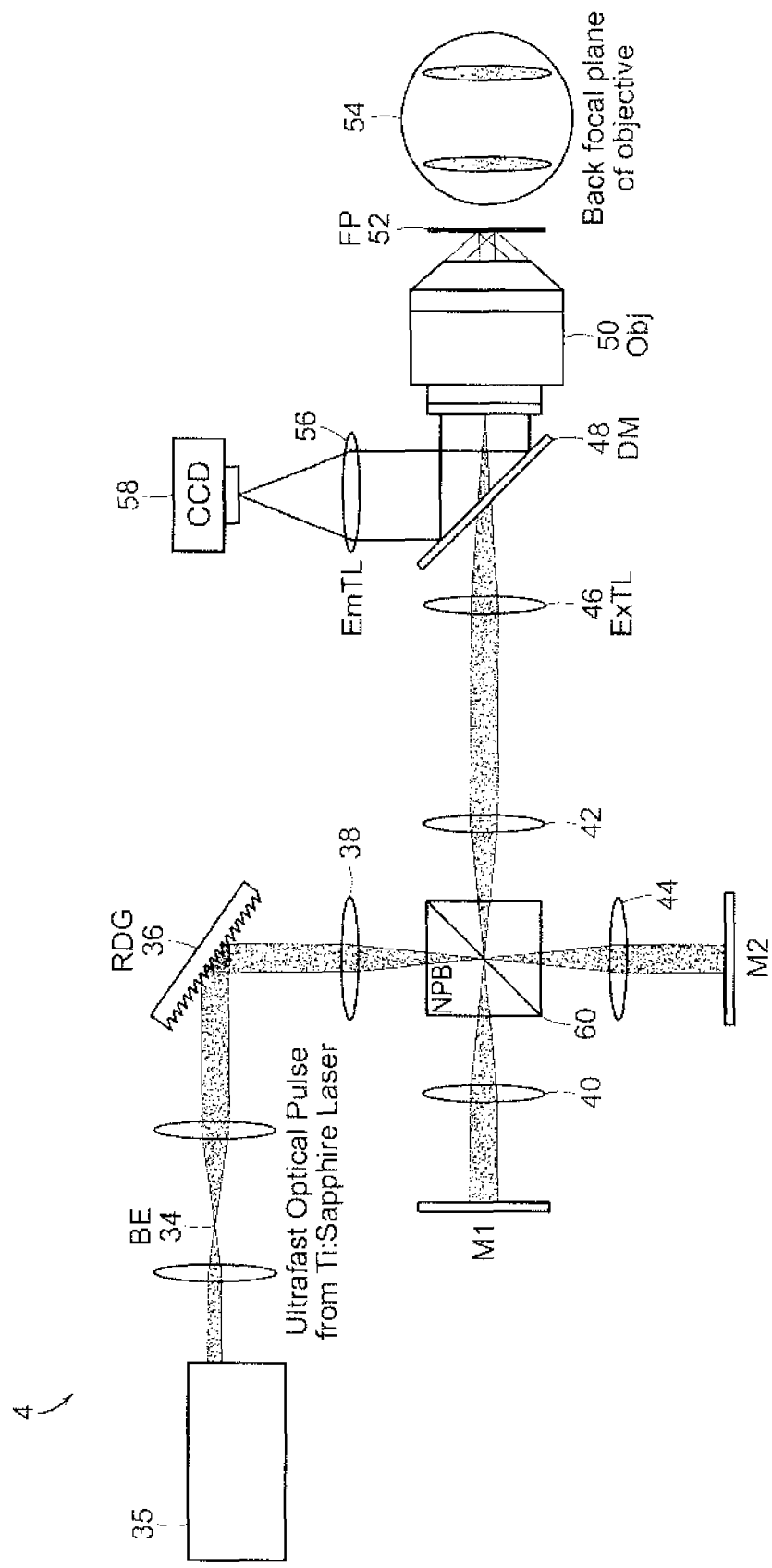

FIG. 1B shows a schematic diagram illustrating an arrangement 4 to form structure light illumination (SI) through interference by combining a temporally focused wide-field 2p microscope with a Michelson interferometer. The arrangement 4 includes a reflective diffractive grating (RDG) 36 that disperse pulsed light received from a beam expander (BE) 34 and a pulsed laser source 35 into a spectrum. The pulsed laser source 35 can include an ultrafast optical Ti:Sapphire laser. A lens structure 38 receives the spectrum from RDG 36 and focuses the spectrum to be received by a non-polarizing beam splitter (NPB) 60. The NPB 60 splits the spectrum into a number of different spectrums which are outputted from a number of ports. In this case, the NPB 60 is positioned at each output port lens structures 40, 42, 44. A mirror M1 reflects the spectrum provided by the lens structure 40 back to the NPB 60. A mirror M2 reflects the spectrum provided by lens structure 44 back through NPB 60. The lens structure 42 provides its respective spectrum to an ExTL 46. The focused spectrum from the ExTL 46 passes thru a DM 48 and is received by an objective 50. The spectrum is then focused at the back focal plane 54 of the objective 50 which collimates each spectral component and recombines them only at the focal plane 52 where the original pulse width is restored.

The group velocity dispersion (GVD) can be tuned to induce a quadratic spectral phase, which effectively shifts the focal plane and thereby creates scanning in the axial direction. A detected signal is relayed back through the objective 50 and separated from the excitation wavelengths by the DM 48 and provide to an EmTL 56. The EmTL 56 focuses the detected signal to a CCD 58 for imaging. Just like the case discussed for FIG. 1A, the absence of a scanning mechanism in the endoscope head allows for the incorporation of the detecting sensor, such as the CCD 58 within the endoscope head itself and increases the signal-to-noise ratio.

For the structured light illumination, the angle of mirrors 1 and 2 are adjusted so that two parallel strips of pulse spectrum are focused at the back focal plane of the objective and interfere at the front focal plane of the objective to generate an interference pattern. For the uniform illumination, one of the beam path to the mirror is blocked.

In temporally focused 2p microscopy, there are two major sources of background. One is the signals originating from out-of-focus planes. The axial resolution of the two photon wide field excitation is about 2 μm and is poorer than the point scanning two photon microscope, which is about 0.8 μm. The other is the scattered emission photon of both in-focus and out-of-focus photons. The latter is more critical in the case of imaging a sample through highly scattering medium.

In FIG. 2A, fluorescent beads (3 μm diameter, Polysciences) dried on a cover slip are imaged to assess the effectiveness of rejecting such background signals with SI. These beads are well characterized and, when dried, occasionally form regions where they form multiple layers. FIG. 2B illustrates the results of applying background rejection where the rejection of the background signal is obvious. From FIG. 2A, emission photons emanating from out-of-focus planes contribute to a constant background, which reduces image contrast and limiting the imaging depth achievable. It is worthwhile to note that this represents an ideal case where there is little scattering because water was used as the immersion medium.

Fixed stained mouse kidney specimen is further imaged through turbid medium with known scattering coefficients. FIG. 3A, 3C, 3E are images taken with no scattering (0%). Even in this case, there is significant background in the normal two-photon wide field image, FIG. 3A. With the addition of structured light illumination, a coarser gird spacing can be used, as shown in FIG. 3C, and using a finer grid spacing as shown in FIG. 3E.

It is clear that the background rejection improves with finer grid spacing but both approaches successfully reduce image background. FIG. 3B, 3D, 3F represent imaging conditions equivalent to imaging through 280 μm of turbid medium with a scattering coefficient of 20 cm$^{-1}$ (comparable to many tissue). FIG. 3B is the 2p wide field image. Similar to the results of the lower scattering case, a finer HiLo grid spacing, as shown in FIG. 3F, provide better background rejection than the coarser case as shown in FIG. 3D. Overall, the application of SI allows a dramatic improvement in the contrast of wide field 2P imaging.

The invention makes it is possible to perform axial scanning at the proximal end of the endoscope thereby making the distal end, the head, of the endoscope much more compact and robust without mechanical moving parts. This is possible because the axial focusing depth of the endoscope is a function of the magnitude of the quadratic chirp—a specific spectral-phase relationship—of the input pulse as shown below.

In the general case of a chirped beam into a temporal focusing microscope, one can express the electric field as at the focal plane as:

$$E5(x_5, dz, \Delta\omega) \approx b_5 \exp\left[-\frac{\left(\eta x_5 + \frac{dz\Delta\omega\eta M\gamma}{k}\right)^2}{\frac{s_0^2}{M^2}}\right] \exp\left[-\frac{A\Delta\omega^2}{4(A^2+B^2)}\right] \times \exp\left[-i\left(\gamma M x_5 \Delta\omega + \frac{dz M^2 \gamma^2}{2k}\Delta\omega^2\right)\right]\exp\left[-i\frac{B\Delta\omega^2}{4(A^2+B^2)}\right] \quad (1)$$

With $$\eta = \frac{\cos\theta_i}{\cos\theta_d}$$

being the astigmatic factor and $\theta_i$ being the angle between the incident beam and the normal of the grating, and $\theta_d$ being the angle of diffraction again with respect to the normal of the grating. $x_5$ is the transverse coordinate; dz is the shift in the axial direction (along the optical axis); $\Delta\omega=\omega-\omega_0$ and is the angular frequency shift away from the central angular frequency $\omega_0$; M is the magnification given by the ratio of the tube lens to the objective focal lengths;

$$\gamma = \frac{2m\pi}{d\omega_0\cos\theta_d};$$

$$k = \frac{2\pi}{\lambda};$$

$$k_x = \frac{2\pi}{\lambda_x};$$

$s_0^2$ is the size of the input beam at the grating; and A and B are parameters associated with the pulse width of the input beam. Other associated variables are m, the diffraction order (here taken as m=−1); d the grating constant; λ the central wavelength; and $\lambda_x$ the wavelength associated with the frequency shift $\Delta\omega$.

The term $$\exp\left[-i\frac{B\Delta\omega^2}{4(A^2+B^2)}\right]$$

is commonly associated with the amount of broadening of the beam as a result of dispersion. From equation 1, this is balanced by the term $$\exp\left[-i\frac{M^2\gamma^2}{2k}dz\right],$$

which represents the amount of shift in the axial direction the temporal focus moves to compensate for the broadening of the beam. From equation 1, it is clear that a chirped input beam causes the temporal focus (position of maximum photon flux) to shift so as to automatically compress the chirped input.

As the endoscope relies on nonlinear optical processes to excite the sample, there is inherent optical sectioning that is related to the numerical aperture (NA) of the objective. In general the axial resolution ($\Delta z$) for a temporally focused two-photon system is related to the NA, field-of-view (FOV), and pulse width ($\tau_p$) by, $$\Delta z = (FOV \times \tau_p)/NA. \quad (2)$$

It can be seen that the larger the NA is, the better the axial confinement. In practice, the NA of the micro objective for the endoscopy is much smaller than the typical microscope objective. In order to increase the optical sectioning performance the proposed invention incorporates structured illumination to the excitation beam path. This is achieved by projecting a fringe pattern onto the object. The rejection of out-of-focus photons can be attained through various means that have been described previously.

The maximum imaged depth is also dependent upon the average power. This is given by, $$z_{max} = l_s \ln\left[\gamma P_{avg} \sqrt{\frac{1}{f\tau}}\right], \quad (3)$$

where $l_s$ is the scattering mean-free-path length, $\gamma$ is related to the collection efficiency as well as the two-photon fluorescence quantum efficiency, $P_{avg}$ is the average power, f is the repetition rate, and $\tau$ is the pulse width.

If the endoscope is operated in the autofluorescence mode (i.e. exciting only the endogenous fluorophores then $\gamma$ is a constant and one can only increase the imaging depth through the average power, repetition rate, and pulse width. The pulse width is a limited variable in the sense that a very short pulse will broaden the pulse to the extent that it no longer excites the fluorophores efficiently. The use of a regenerative amplifier is also advantageous as it can increase the signal-to-noise ratio considerably. At the same time it is possible to use extrinsic two-photon probes that have large cross-sections. Such probes include quantum dots and conjugated polymer nanoparticles. In the proposed invention, wide-field multiphoton imaging has low excitation efficiency in the autofluorescence mode and there are a number of competing design requirements including the image field of view (L) and the available laser average power ($P_0$). These two parameters are related to the multiphoton absorption probability, Pr, (measured as photon pairs absorbed per molecule per laser pulse):

$$Pr \propto \delta \left(\frac{\lambda}{hc}\right)^2 \frac{p_o^2}{f^2\tau} \frac{1}{L^4} \quad (4)$$

Where $\delta$ is the multiphoton cross section, $\lambda$ is the excitation wavelength (assume to be $8 \times 10^{-7}$ m), h is the Planck's constant, c is the speed of light, $p_0$ is the average power (assumed to be 2 W), $\tau$ is laser pulse width (assumed to be $1 \times 10^{-13}$ s), f is the laser repetition rate (assumed to be 80 MHz), and L is the linear dimension of the exposure area. In general, maximizing the multiphoton absorption probability maximizes fluorescence signal produced from a fluorophore. However, when multiphoton excitation probability becomes too large, image resolution degrades due to excitation saturation.

The compromised optimal value for Pr is about 0.1. Consider a typical fluorophore with multiphoton cross section of 40 GM ($40 \times 10^{-58}$ m$^4$ s) and keeping Pr at 0.1, $8 \times 8$ $\mu$m$^2$ is the largest area that can be imaged with a $P_0$ of 2 W, the maximum power produced by typical titanium-sapphire lasers. This area is clearly too small for useful endoscopy imaging. This difficulty can be partly alleviated by using multiphoton fluorophores with significantly higher cross section such as quantum dots and conjugated polymer particles, that have cross sections on the order 10,000 GM. With these higher contrast agents of larger cross sections, the size of the image area can be improved to over $32 \times 32$ $\mu$m$^2$.

Further improvement can be obtained by using a regenerative amplifier that reduces laser pulse repetition rate while maintaining pulse width and laser average power. For a regenerative amplifier system with 1 KHz repetition rate, an image area up to $1.6 \times 1.6$ mm$^2$ can be achieved in theory. However, without the costly parametric amplifier, the need for high multiphoton cross section contrast agent is particularly paramount if a larger imaging area is desired. For a $150 \times 150$ $\mu$m$^2$ image area, it is clearly impossible to optimally excite fluorophores with a typical Ti-Sapphire laser at 2 W average power. The maximum multiphoton absorption probability that can be achieved is $3.8 \times 10^{-4}$ and $1.5 \times 10^{-6}$ for fluorophores with cross sections of 10,000 GM and 40 GM respectively. For these two cases, the numbers of fluorescent photons produced per second per molecule are 30,400 and 120 assuming 100% quantum efficient and no tissue absorption or scattering. For imaging at a rate of 100 ms and assuming microscope detection efficiency of 5%, the numbers of molecules per pixel of 200, the achievable signal-to-noise ratios are 174 and 11 respectively. Certainly, the fluorophore with larger multiphoton cross sections will be advantageous for the video rate imaging.

With regards to using high energy, high peak power pulsed beams, two issues need to be addressed. One is the potential thermal damage to the tissue and the other is the delivery of high peak pulses to the remote imaging area. High intensity laser illumination increases the local temperature and potentially induces local tissue thermal denaturation. Local maximum temperature increase come from both a cumulative effect (first term of equation 5) and a single pulse effect (second term of equation 5).

$$T_{max} = \left[\frac{\mu_a E f_p}{4\pi k_t}\ln\left(1 + \frac{2t_{res}}{\tau_c}\right)\right]\left[\frac{\mu_a E}{2\pi k_t \tau_c}\right] \quad (5)$$

where $\mu_a$ is the thermal absorption coefficient, E the single pulse energy, $f_p$ the pulse repetition rate, $k_t$ thermal conductivity, $t_{res}$ exposure time, and $\tau_c$ thermal time constant. Consider imaging an area of $128 \times 128$ $\mu$m$^2$ in size where the major absorber is water. For a titanium-sapphire oscillator with an input power of 2 W and a repetition rate of 80 MHz, the majority of the temperature increase comes from the cumulative effect of one-photon absorption that is about 1.8 K since $\tau_c$ is 7 ms, which is relatively longer than the time between the pulses. Single pulse effect corresponds to only a 1.9 $\mu$K temperature rise. However, if a regenerative amplifier with a repetition rate of 1 kHz is used, the input power required to achieve Pr of 0.1 becomes only 7 mW. In this case, the temperature increases due to the cumulative effect is only 6.3 mK and that due to the single pulse effect is 0.52 mK. One can see that the thermal issue is minimal in the case of an oscillator and is negligible for the regenerative amplifier case. From equation 4, one can further estimate the excitation efficiency of using a regenerative amplifier over that of a titanium-sapphire oscillator. Assuming the imaging system is shot noise limited, both systems will give the same signal to noise ratio at each pixel using the power levels proposed, whereas the regenerative amplifier allows the imaging of a much larger area.

Delivering high peak pulse through the silica fiber induces complex nonlinear effects such as self-focusing that can damage the fiber. In the case of a 1 KHz regenerative amplifier, the single pulse energy can reach up to 7 µJ for Pr of 0.1. There are a number of groups who have designed a hollow core fiber for the high peak energy delivery. It has been shown that 100 fsec with 1 KHz repetition rate Ti-Sapphire laser with pulse energies of up to 300 µJ can be delivered through a silver coated hollow waveguide without damage to the optical fiber. It should be noted that for endoscope imaging, the pulse energy required is only 7 µJ, significantly below the power delivery threshold demonstrated by these groups.

Figure 4:
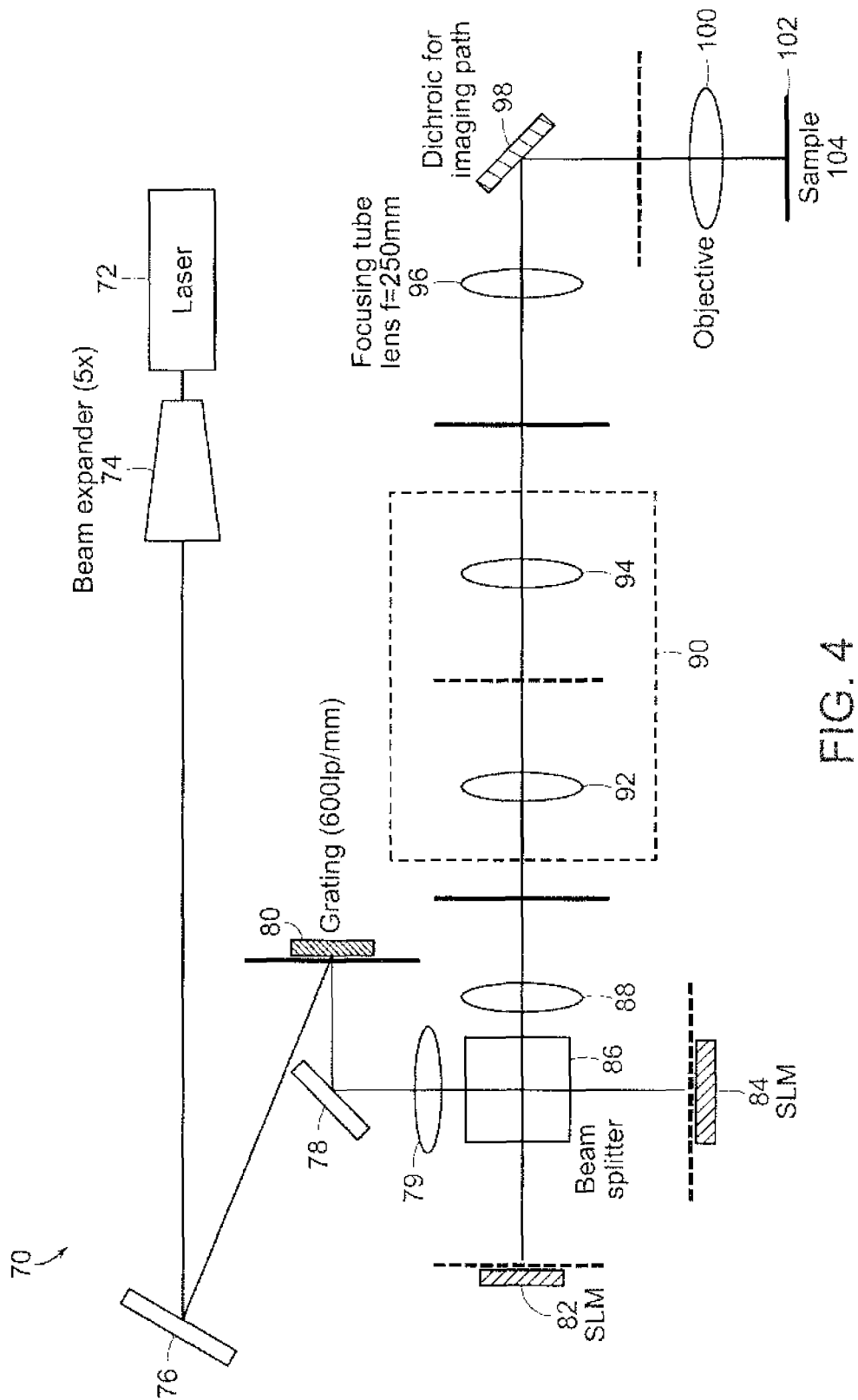
FIG. 4 is a schematic diagram illustrating an arrangement to produce 2p wide field illumination.

A temporal focusing microscope 70 setup is shown in FIG. 4. The temporal microscope 70 includes a laser source 72 that provides pulsed light to a beam expander 74, which forwards an expanded pulsed beam to a mirror structure 76 that reflects the expanded pulsed beam to a grating structure 80. The grating structure 80 disperses the expanded pulsed beam into a spectrum that is provided to a mirror structure 78. The mirror structure 78 reflects the spectrum to a lens structure 79 that focuses the spectrum to be sent to a beam splitter 86. Positioned at selective outputs of the beam splitter 86 are spatial light modulators (SLMs) 82, 84. The SLMs 82, 84 received from the beam splitter 86 a spectrum which is then is reflected back into the beam splitter 86. Moreover, the beam splitter 86 includes an output providing a spectrum to a lens structure 88 that focuses the spectrum into a dispersive element 90. The dispersive element 90 includes lens structures 92, 94 placed at their respective focal lengths to form a 4-f system and functions as a control the size of the beam size as well as the spectral spread at the back focal plane of the objective. The spectrum received by the dispersive element 90 is further dispersed when passing thru the lens structures 92 and 94. The spectrum produced by the dispersive element 90 is provided to ExTL 96. The focusing tube lens 96 focuses the received spectrum to a dichroic filter element 98 that serves to separate the excitation light from the emission light. In this representation, it reflects the excitation beam before being focused at the back focal plane an objective 100. The spectrum is then focused at the back focal plane 102, and a sample 104 is positioned within the focus of the objective 100, which collimates each spectral component and recombines them only at the focal plane 100 where the original pulse width is restored.

For the structured light illumination, the angle of SLMs 82, 84 are adjusted so that two parallel strips of pulse spectrum are focused at the back focal plane 102 of the objective 100 and interfere at the front focal plane of the objective 100 to generate an interference pattern. For the uniform illumination, one of the beam paths to either SLMs 82 or 84 is blocked.

Figure 5:
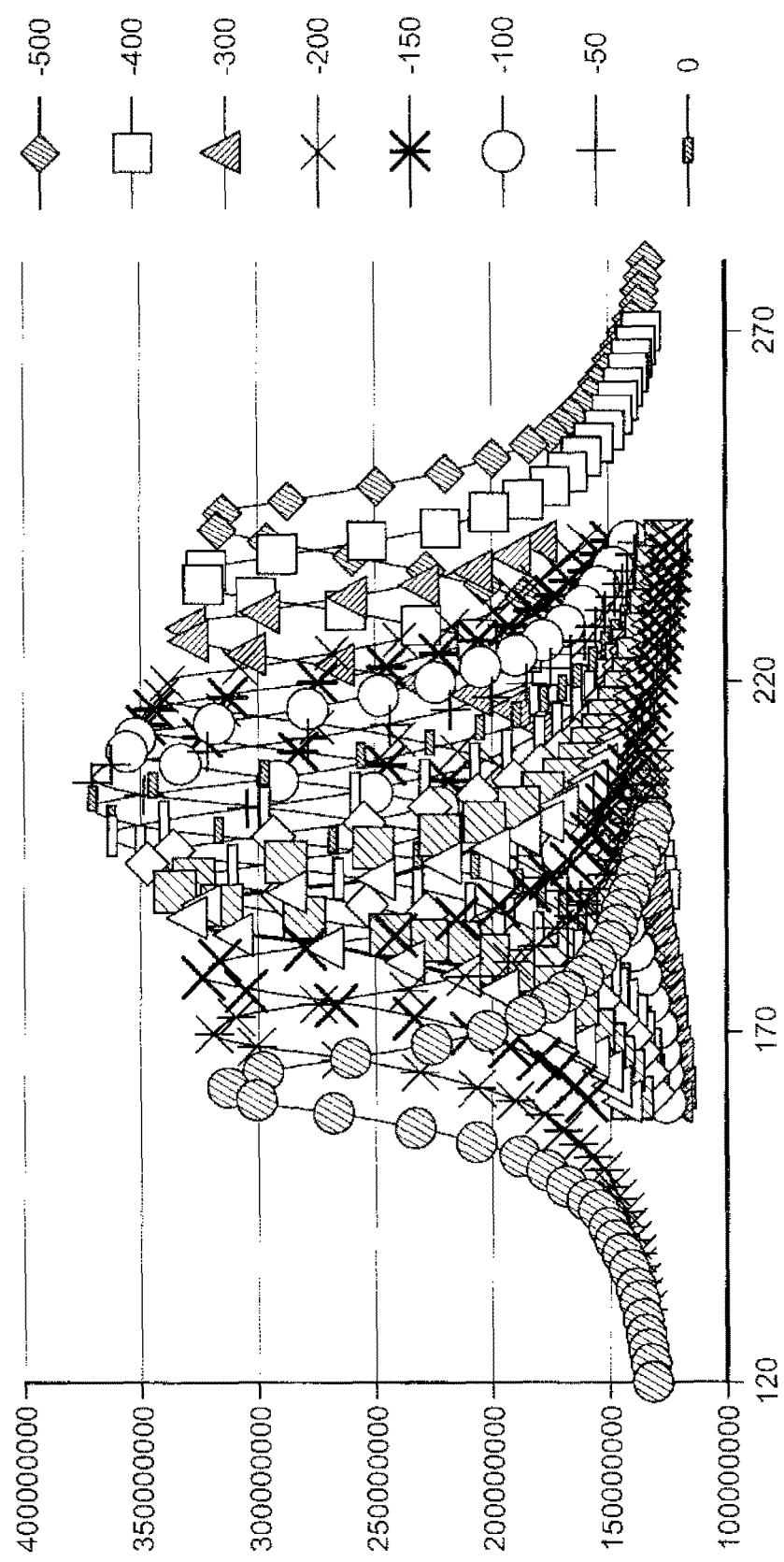
FIG. 5 is a graph illustrating variation of the fluorescence signal strength along the optical axis from the illumination produce from the arrangement in FIG. 4.

To control the chirp of the beam from the laser source 72 the SLMs 82, 84 are phase-only spatial light modulators placed at the Fourier plane of lens structure 79. A quadratic phase may be written independently to the SLMs 82, 84. Each input pulsed beam to the SLMs 82, 84 will therefore form an independent plane in the sample 104 that is temporally focused at a certain axial depth related to the spectral phase (linear chirp) written to the respective SLMs 82, 84. In this manner both planes can be shifted to the same axial position and interfered with each other to generate structured illumination for 2p wide field excitation as described earlier. A thin layer of Rhodamine 6G was used as the sample 104 and mounted on a piezostage with sub-micron resolution. At each chirp value, the thin layer of Rhodamine was translated over a distance of 80 microns along the optical axis and the signal recorded on a charged coupled device camera. The variation of the fluorescence signal strength along the optical axis is shown in FIG. 5.

Photon reassignment technique is developed for 3D visualization of biological tissues utilizing structured light widefield microscopic imaging system. This method provides the capability to image deeper into biological tissue by reassigning fluorescence photons generated from off-focal plane excitation improving in-focus signal strength. Existing structured light illumination based methods allowing widefield visualization of the focal plane while rejecting out-of-focus background "haze". While these techniques are able to improve image contrast, the loss of out-of-focal plane photons limits the final image signal-to-noise ratio (SNR).

Additionally, if the contrast of the projected grid is low this reduces the modulation and provides the weaker sectioning capability and as a result reduces the photons of the reconstructed optically sectioned image. The photon reassignment technique seeks to better utilize the lost photons by using the 'prior knowledge' about the optical transfer function of the structured light illumination. By utilizing a maximum likelihood approach, the most likely fluorophores distribution in 3D can be identified that will produce the observed image stacks under structured and uniform illumination using an iterative maximization algorithm. The accuracy of the reconstruction partly depends on the smoothness of initial estimate chosen and the constrained parameters for convergence of the algorithm.

Figure 6B:
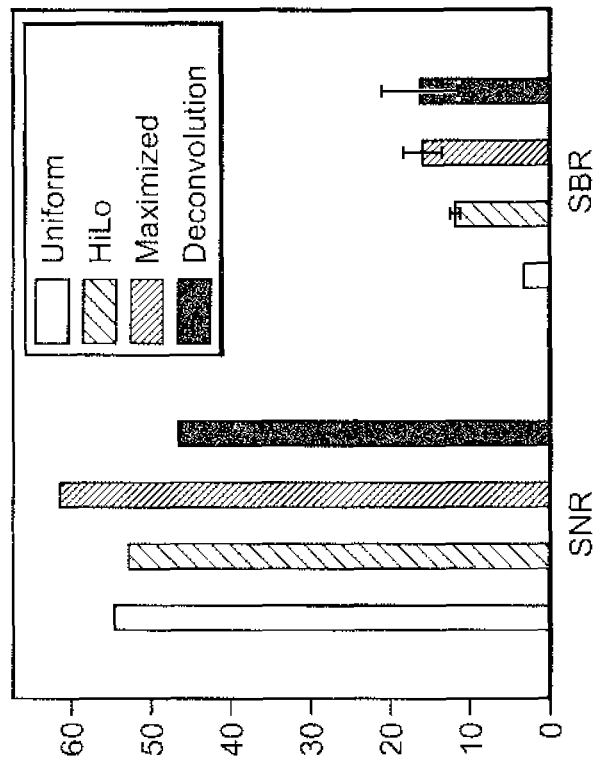
FIGS. 6A-6B are graphs illustrating analysis of in-focus signal and background illumination as well as SNR and SBR analysis based on the incorporation of structured illumination and photon reassignment methods.
Figure 6A:
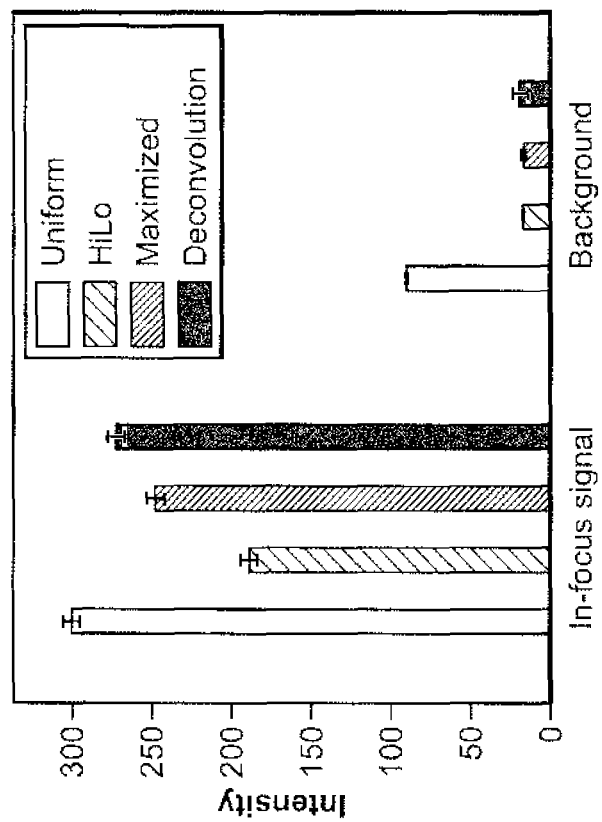

Performance of the proposed method was first evaluated with a z-stack of wide-field fluorescence images of fluorescence beads. Results show that this approach provides comparable background rejection as existing structured light imaging methods, such as HiLo microscopy, while improving final image SNR. The analysis of reconstruction results are quantitatively compared with the images acquired using HiLo and deconvolution methods, as shown in FIG. 6A, and evaluation of SNR and signal-to-background ratio (SBR) were performed, as shown in FIG. 6B. It was observed that the inventive technique improves the SNR and SBR of the reconstructed images compared to the existing structured illumination based method (HiLo) and deconvolution. Furthermore, when compared to wide-field images, the contrast and SBR improvement is significant improved for the photon reassigned image, as shown in FIGS. 6A-6B.

Figure 7A:
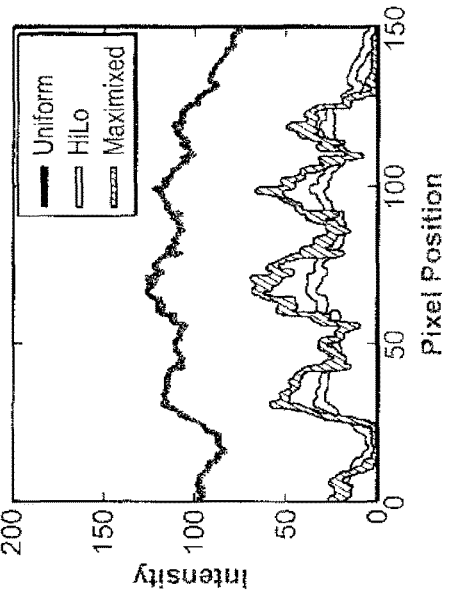
FIGS. 7A-7F are wide field fluorescence uniform images of zebrafish intestine and the corresponding reconstructed images using structured illumination and photon reassignment for tissue at different axial positions as well as the line profile of intensity values.
Figure 7B:
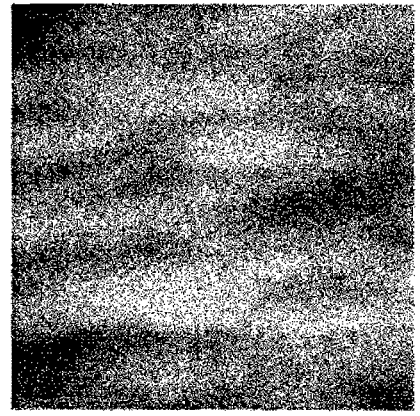
Figure 7C:
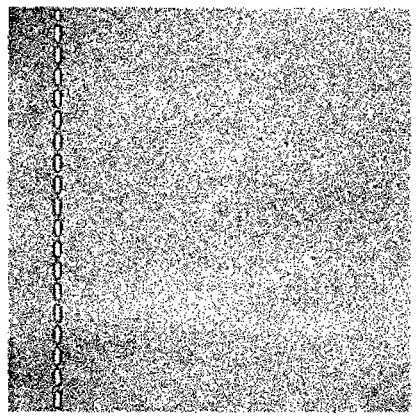
Figure 7D:
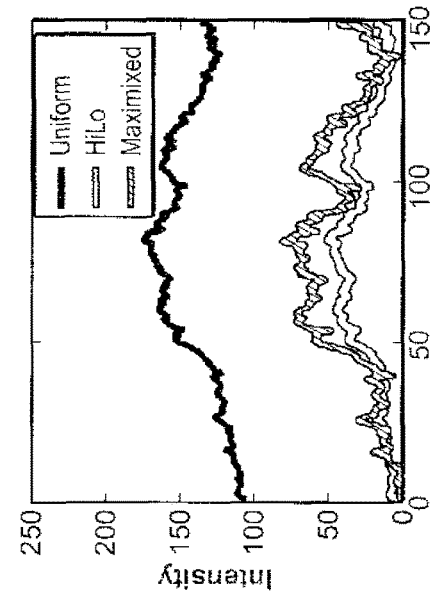
Figure 7E:
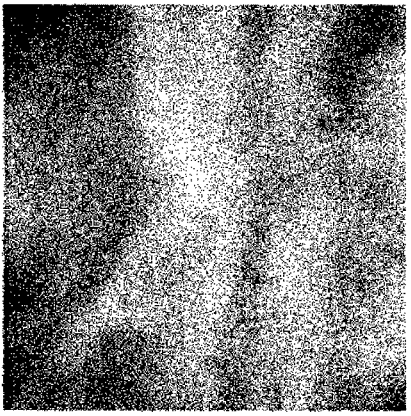
Figure 7F:
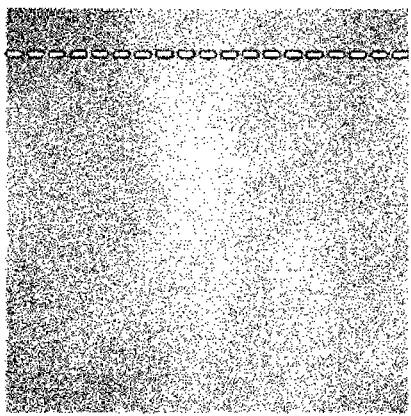

The proposed method is further used for the imaging analysis of fluorescently stained zebrafish intestine tissue sample. It is important to note, due to high scattering effect, the contrast of projected grid reduces with an increase in sample depth. This reduces the modulation and provides the weaker sectioning capability for structured light based image processing. The reassignment of the photons using the proposed approach is thus particularly significant in such situation. In particular, FIGS. 7A and 7D show the wide field fluorescence uniform images of zebrafish intestine. FIGS. 7B and 7E are the corresponding reconstructed images, for tissue at different axial positions. FIGS. 7C and 7F shows the line profile of intensity values.

The presented photon reassignment technique provides significantly fast reconstruction of volumetric data compared to existing deconvolution methods. More importantly, it provides the actual 3D structure with better fidelity than deconvolution method as the axial information is not lost in the optical transfer function of structured illumination microscopy. Results show the significant optical sectioning capability of tissue sample while preserving the photons count, which is usually not achievable with other existing structured light imaging methods.

For even deeper imaging, it is known that a majority of the detected image photons originates from the surface layer due to scattering of the excitation light and generate a significant non-depth resolved background. Structured light illumination and photon reassignment partly solves this problem. In such case the diffuse out-of-plane signal is much stronger than the in-focus structured light signal. The contrast of the projected grid is lost and this limits the applicability of the structured illumination based methods. To overcome such limitation and make the system capable for deeper imaging applications, grid modulation based lock-in detection method can be used to detect very small level in-focus singles subjected to strong background noise. The structured light distribution will be periodically and spatially shifted at a given temporal frequency. Since only in-focus signal retains structured light information and will be modulated in time and the out-of-focus signal is mostly spatially uniform and will not be modulated in time, a locked-in detection of the temporally modulating signal will allow us to improve the SNR between the in-focus vs out-of-focus signals upon averaging. In principal, the contrast of the structured light can be improved to the shot-noise limit allowing even deeper imaging.

Figure 8:
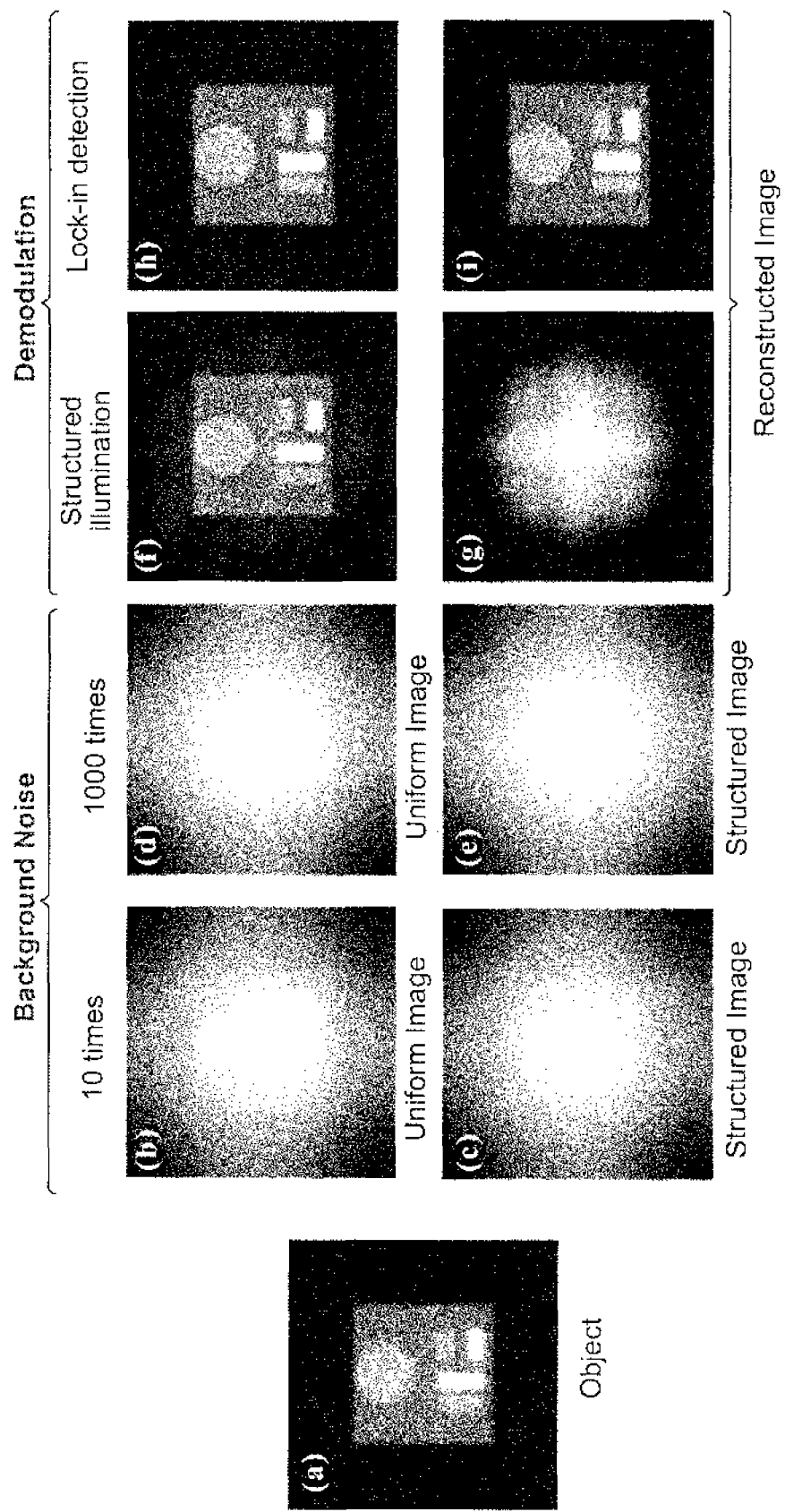
FIGS. 8A-8I is a simulation of SNR improvement by locked-in detection of the spatially and periodically shifting the structured illumination in time.

The validation of grid modulation based lock-in detection is performed using simulations. The results are shown in FIG. 8(a)-8(i). Object was simulated showing the in-focus information (signal) as shown in FIG. 8(a). The background (noise) is added in the in-focus image by two different amount (10 times and 1000 times), shown in FIGS. 8(b)-8(e). Clearly, increase in the background noise reduces the grid contrast and results as the non-resolved signal noise for higher background noise, as shown in FIGS. 8(f)-8(g). The grid modulation (100 cycles) is performed for four phase step and the effective recovery of the signal are clearly observed as shown FIGS. 8(h)-8(i).

Figure 9:
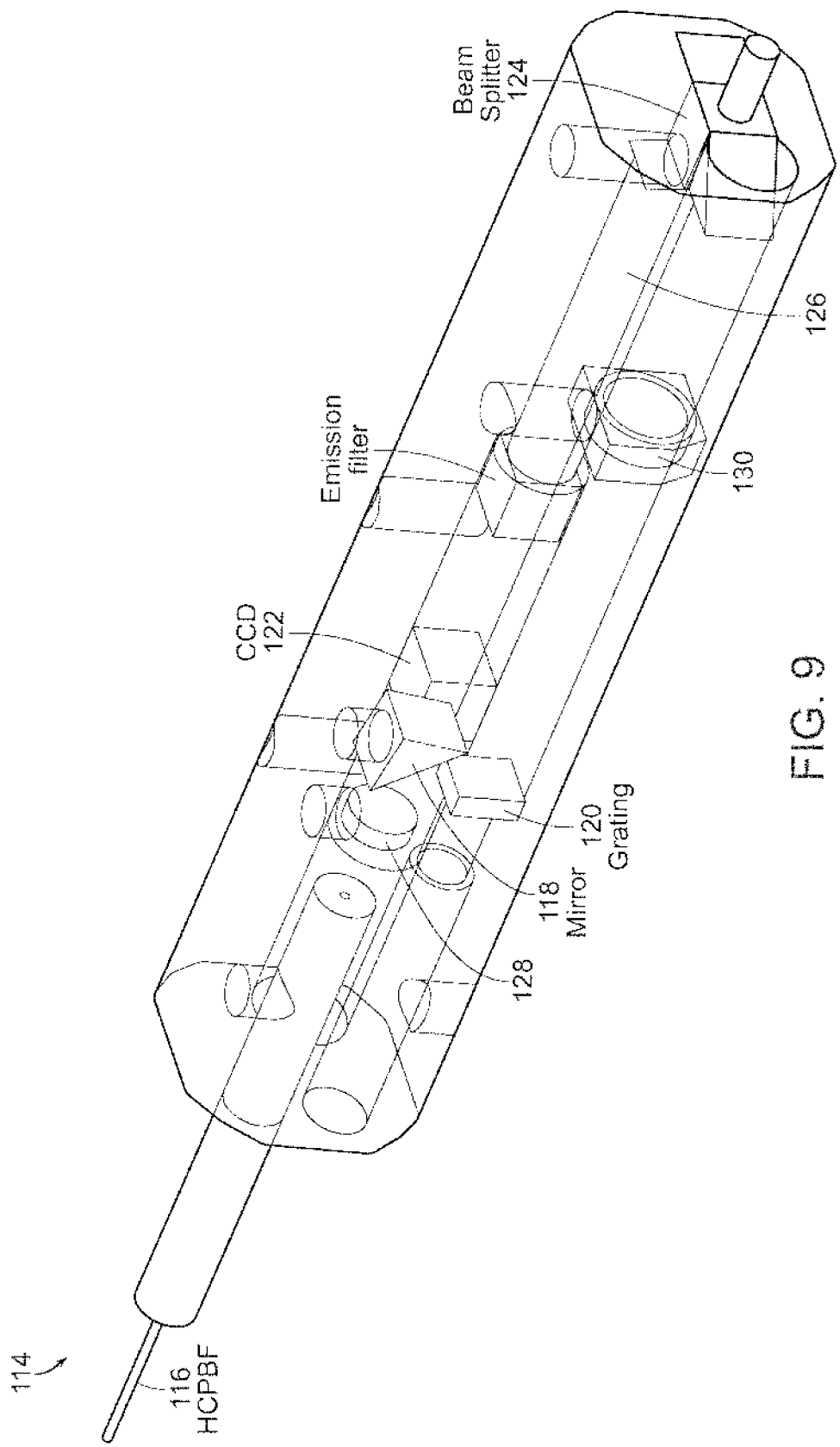
FIG. 9 is a schematic diagram illustrating a partial assembled device formed in accordance with invention.

FIG. 9 shows the optical design of a temporal focusing miniaturized microscope found in accordance with the invention using Zemax and SolidWorks. Femtosecond excitation pulses are delivered through air guiding photonic bandgap fiber 116 (Thorlabs, HC-800B—Hollow Core PCF, 820 nm, Ø7.5 μm Core) which minimize the effect of the dispersion of the pulse and has high threshold power for nonlinear effects. The input beam is collimated by collimating lens 128 (Edmund Optics, NT65-308, f=3 mm, Ø2 mm) and reflected by a right angle prism mirror 118 (Edmund Optics, NT45-524, 2 mm) with the gold mirror coating (Evaporated Coatings Inc) to a reflective grating 120 (LightSmyth, 1200 line/mm, 2 mm×2 mm). The grating 120 is custom-made so that the first order diffraction is maximized for the excitation wavelength at 800 nm. The input pulses are spectrally dispersed by the grating 120 and focused by a focusing lens 130 (Edmund Optics, NT45-964, f=12 mm, Ø3 mm) at the back aperture of the 1 mm GRIN objective 126 that collimates each spectral component and recombines them at the focal plane of the objective 126 to restore original input pulse width.

This spatio-temporally focused beam induces two-photon excitation only around the focal plane of the objective 126. Thus, the depth resolved 3D images can be obtained. The image from the focal plane is magnified and relayed through GRIN lens and beam cube splitter block 124 and detected by a 1/10" size CCD camera 122 at the distal end directly. The dichroic filtering is performed by an emission filter 124 prior to detection by the CCD camera 122. Alternatively, a higher sensitivity design may utilize an image preserving fiber optics bundle that may take the image from the distal end to a high sensitivity, cooled CCD camera 122 at the proximal end. The GRIN lens and beam cube splitter block 124 was custom-fabricated by GRINTECH. The current fabricated housing size is 8 mm but if it can be reduced to 5 mm in diameter, it can be fitted into the diagnostic channel of a commercial gastroenterological endoscope. Depth scanning will be accomplished by tuning the group velocity dispersion at the proximal end. In this way, one can remove the actuator at the proximal end and can make the imaging device more compact and robust.

The invention has successfully demonstrated that scattered photons can be efficiently rejected with structured light illumination. Some of these rejected scattered photons can be "saved" by reassigning them to the correct image location using a maximum likelihood algorithm further improving image signal-to-noise level (SNR). Moreover, scanning along all three axes can be eliminated from the distal end of an endoscope by showing that axial scanning can be readily accomplished by varying the spectral-phase relationship of the excitation pulses. Axial scanning based on this approach has been shown by other groups but the invention has implemented this approach using a spatial light modulator allowing more facile depth control. More importantly, multiple planes can be simultaneously excited and imaged at the same time. The capability of simultaneously imaging a volume (not just a single plane) is an important new feature. Finally, the miniaturization of the inventive system using micro-optics in an "open" design has been demonstrated. An enclosed design with a form factor less than 8 mm in diameter has been implemented as well.

Although the present invention has been shown and described with respect to several preferred embodiments thereof, various changes, omissions and additions to the form and detail thereof, may be made therein, without departing from the spirit and scope of the invention.

What is claimed is:

1. An imaging system comprising:
   a pulsed light source that provides pulsed light;
   one or more dispersive elements that are positioned to receive the pulsed light and apply selective dispersive properties to recombine the spectrally dispersed pulse at a certain position along the optical axis where with the recombined pulse, a sequence of two photon (2p) wide field uniform illumination and 2p wide field structured illumination is generated at the focal plane; and
   an imaging element that receives multiple 2p wide field uniform illumination and 2p wide field structured illumination images to produce respective 3D resolved images of a sample, wherein the group velocity dispersion (GVD) of the pulsed light is tuned to induce a quadratic spectral phase, which effectively shifts the focal plane and thereby allows scanning in the axial direction of the pulsed light.

2. The imaging system of claim 1, wherein the pulsed light source comprises a laser and a beam expander of variable magnification.

3. The imaging system of claim 1, wherein the one or more dispersive elements disperses the pulsed light to form a spectrum.

4. The imaging system of claim 1, wherein the image element comprises an objective which collimates each spectral component associated with the uniform illumination and 2p wide field illumination and recombines them at a focal plane where the original pulse width of the pulsed light is restored.

5. The imaging system of claim 1, wherein the pulsed light are positioned at a focal plane thereby generating high peak power and increasing the probability of a multiphoton process occurring while maintaining a wide field of view.

6. The imaging system of claim 1, wherein the 2p wide field illumination permits axial scanning at the operator end of an endoscope, which reduces the size of the endoscope head.

7. The imaging system of claim 1, wherein the 2p wide field illumination permits axial scanning at the operator end of an endoscope through the control of the spectral phase of the input pulsed beam.

8. The imaging system of claim 1, wherein the image element comprises a detector being located within an endoscope head allowing the signal-to-noise ratio to increase.

9. A method for performing deep tissue imaging through improving the optical sectioning as well as the rejection of background signal comprising:
providing a pulsed light source that provides pulsed light;
positioning one or more dispersive elements to receive the pulsed light and apply selective dispersive properties to recombine the spectrally dispersed pulse at a certain position along the optical axis where with the recombined pulse a sequence of two photon (2p) wide field uniform illumination and 2p wide field structured illumination is generated at the focal plane; and
receiving multiple 2p wide field uniform illumination and 2p wide field structured illumination images to produce respective 3D resolved images of a sample using an imaging element, wherein the group velocity dispersion (GVD) of the pulsed light is tuned to induce a quadratic spectral phase, which effectively shifts the focal plane and thereby allows scanning in the axial direction of the pulsed light.

10. The method of claim 9, wherein the pulsed light source comprises a laser and a beam expander.

11. The method of claim 9, wherein the one or more dispersive elements disperses the pulsed light to form a spectrum.

12. The method of claim 9, wherein the image comprises using images formed using the 2p wide field uniform illumination and 2p wide field structured illumination.

13. The method of claim 9, wherein the imaging element comprises focusing the dispersed spectrum at the back focal plane of an objective, which collimates each spectral component associated with the 2p wide field uniform illumination and 2p wide field structured illumination and recombines them at a focal plane where the original pulse width of the pulsed light is restored.

14. The method of claim 9, wherein the pulsed light are positioned at a focal plane thereby generating high peak power and increasing the probability of a multiphoton process occurring while maintaining a wide field of view.

15. The method of claim 9, wherein the 2p wide field illumination permits axial scanning at the operator end of the method, which reduces the size of the method head.

16. The method of claim 9, wherein the image element comprises a detector being located within the method head allowing the signal-to-noise ratio to increase.

17. The method of claim 9, wherein the 2p wide field uniform illumination and 2p wide field structured illumination are capable of being used as background rejection techniques to improve optical sections in the axial direction.

18. The method of claim 9 further comprising combining the multiple uniform wide-field 3D resolved two-photon illumination images and multiple structured wide-field 3D resolved two-photon illumination images for rejection of out-of-focal noise from in-focus signal using a computer algorithm.

19. The method of claim 9, wherein a computational algorithm of photon reassignment based on maximum likelihood estimation applied for 3D image reconstruction from a z-stack of uniform and structured wide-field 3D resolved two-photon illumination images to improve image stack signal-to-noise (SNR) level.

20. The method of claim 9, wherein the structured illumination is periodically and spatially shifted in time.

21. The method of claim 20, wherein the structured illumination is lock-in detected at the period of the shifting of the structured light pattern allowing shot-noise limited detection of structured illumination imaging increasing its contrast.

* * * * *